(12) United States Patent
Gurley

(10) Patent No.: US 7,546,657 B2
(45) Date of Patent: Jun. 16, 2009

(54) CLEANING TOOL FOR MOBILE ELECTRONIC DEVICES

(76) Inventor: Karen Gurley, 3461 Lantern View La., Scottdale, GA (US) 30079

( * ) Notice: Subject to any disclaimer, the term of this patent is extended or adjusted under 35 U.S.C. 154(b) by 0 days.

(21) Appl. No.: 11/542,868

(22) Filed: Oct. 4, 2006

(65) Prior Publication Data

US 2007/0074360 A1    Apr. 5, 2007

Related U.S. Application Data

(60) Provisional application No. 60/723,868, filed on Oct. 5, 2005.

(51) Int. Cl.
*A47L 25/00* (2006.01)
(52) U.S. Cl. .................. 15/118; 15/104.94; 15/210.1
(58) Field of Classification Search .............. 15/104.94, 15/118, 209.1, 210.1, 214, 244.1; 206/361, 206/362; 604/1
See application file for complete search history.

(56) References Cited

U.S. PATENT DOCUMENTS

| | | | | |
|---|---|---|---|---|
| 2,006,539 A * | 7/1935 | Deford | ........................... | 604/1 |
| 2,510,961 A * | 6/1950 | Davis | ........................... | 604/1 |
| 3,759,375 A * | 9/1973 | Nappi | ........................ | 206/362 |
| 4,065,801 A * | 12/1977 | Leaming | ..................... | 360/137 |
| 4,887,994 A * | 12/1989 | Bedford | ......................... | 604/1 |
| 4,934,011 A * | 6/1990 | Haug | ........................... | 15/145 |
| 5,148,572 A * | 9/1992 | Wells et al. | .................. | 15/118 |
| 5,738,643 A * | 4/1998 | Stredic, III | ..................... | 604/1 |
| 5,991,960 A * | 11/1999 | Johnson | ..................... | 15/210.1 |
| 6,052,858 A * | 4/2000 | Drakulic | .................... | 15/244.2 |
| 6,134,742 A * | 10/2000 | Fernando et al. | .............. | 15/231 |
| 6,185,778 B1* | 2/2001 | Ornstedt | ...................... | 15/114 |
| 6,277,090 B1* | 8/2001 | Crawford, Jr. | .................. | 604/1 |
| 6,601,264 B1* | 8/2003 | Hendricks | ................... | 15/244.1 |
| 6,629,329 B1* | 10/2003 | Webb et al. | ................ | 15/209.1 |
| 2006/0156501 A1* | 7/2006 | Grunberger | ............... | 15/209.1 |

* cited by examiner

*Primary Examiner*—Mark Spisich
(74) *Attorney, Agent, or Firm*—James Ray & Assoc.

(57) ABSTRACT

A cleaning tool for cleaning mobile electronic devices includes a base member which is manufactured from a first predetermined material and which has a cleaning portion and an elongated handle portion which is attached to and extends from the cleaning portion. A cleaning member is manufactured from a second predetermined material and is attached to the cleaning portion. As second cleaning member may be attached to a free end of the handle portion which is preferably tapered.

4 Claims, 1 Drawing Sheet

CLEANING TOOL FOR MOBILE ELECTRONIC DEVICES

CROSS-REFERENCE TO RELATED APPLICATIONS

This application is related to and claims priory from Provisional Patent Application Ser. No. 60/723,868 filed Oct. 5, 2005.

FIELD OF THE INVENTION

The present invention relates, in general, to cleaning tools and, more particularly, this invention relates to a cleaning tool for mobile electronic devices such as phones, pagers, iPod players, mp3 players, Personal Digital Assistants, cameras and the like.

BACKGROUND OF THE INVENTION

Many individuals are known to clean the delicate display screen or a camera lens on their mobile electronic device against a portion of the clothing in order to remove dirt, dust and finger prints. Such ineffective method often fails to produce desired results as the fabric particles are left on such display screen or camera lens. Furthermore, conventional clothing fabric is often made from synthetic fibers which can scratch or harm the display screen or camera lens.

It is furthermore known that facial tissue is not suitable for cleaning the display screen or the camera lens due to containing abrasive particles and undesirable lubricants or oils.

There is a need for a cleaning tool which enables effective and safe cleaning of display screens and camera lens on a mobile electronic device.

SUMMARY OF THE INVENTION

The invention provides a cleaning tool for cleaning mobile electronic devices. The cleaning tool includes a base member which is manufactured from a first predetermined material. The base member has a cleaning portion and an elongated handle portion which is attached to and extends from the cleaning portion. A cleaning member is manufactured from a second predetermined material and is attached to the cleaning portion.

OBJECTS OF THE INVENTION

It is, therefore, one of the primary objects of the present invention to provide a cleaning tool for mobile electronic devices.

Another object of the present invention is to provide a cleaning tool for mobile electronic devices which will not scratch or harm display screen and camera lens contained therein.

Yet another object of the present invention is to provide a cleaning tool for mobile electronic devices which enables quick and effective cleaning of such devices.

A further object of the present invention is to provide a cleaning tool for mobile electronic devices which is simple to use.

Yet a further object of the present invention is to provide a cleaning tool for mobile electronic devices which is economical to manufacture.

An additional object of the present invention is to provide a cleaning tool for mobile electronic devices which employs cotton fibers for cleaning such devices.

In addition to the several objects and advantages of the present invention which have been described with some degree of specificity above, various other objects and advantages of the invention will become more readily apparent to those persons who are skilled in the relevant art, particularly, when such description is taken in conjunction with the attached drawing Figures and with the appended claims.

BRIEF DESCRIPTION OF THE VARIOUS EMBODIMENTS OF THE INVENTION

Figure 1:
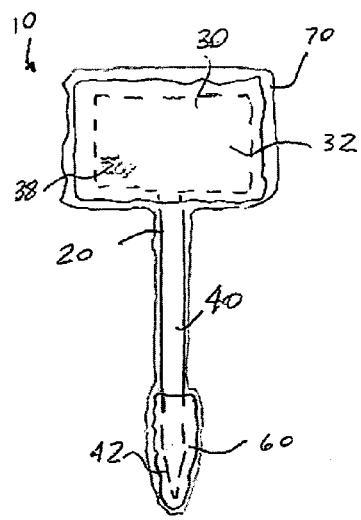
FIG. 1 is a planar view of a cleaning tool for mobile electronic devices, constructed according to one embodiment of the invention.

Prior to proceeding to the more detailed description of the present invention, it should be noted that, for the sake of clarity and understanding, identical components which have identical functions have been identified with identical reference numerals throughout the several views illustrated in the drawing figures.

It is to be understood that the definition of a mobile electronic device includes but is not limited to phone, pager, music player, video player, Personal Digital Assistant (PDA) and the like.

Figure 2:
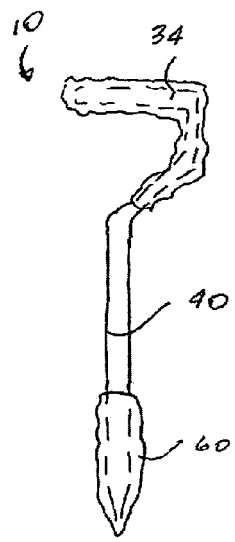
FIG. 2 is a planar view of the cleaning tool for mobile electronic devices, constructed according to another embodiment of the invention.
Figure 3:
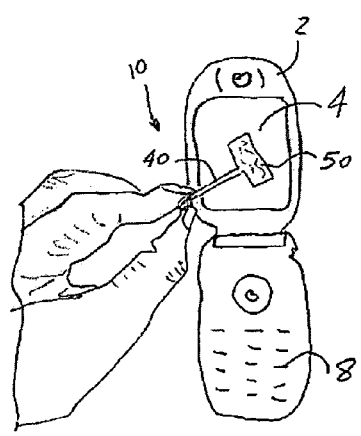
FIG. 3 is a planar view of the cleaning tool of FIG. 1 illustrated in use for cleaning a display screen of such mobile electronic device.
Figure 4:
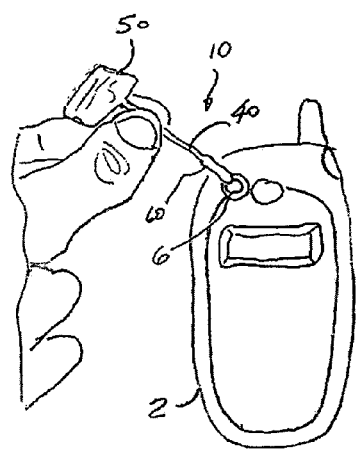
FIG. 4 is a planar view of the cleaning tool of FIG. 1 illustrated in use for cleaning a camera lens of such mobile electronic device.

Reference is now made, to FIGS. 1-5, wherein there is shown a cleaning tool, generally designated as 10, for cleaning mobile electronic devices 2. The cleaning tool 10 includes a base member 20 which is manufactured from a predetermined material including but not limited to plastic, tubular plastic, wood, rolled paper and various combinations thereof. The base member 20 includes a first cleaning portion 30 which has a predetermined shape and which is employed for cleaning a generally rectangular display screen 4 of the mobile electronic device 2, as best shown in FIG. 3. The size of the cleaning portion 30 will be preselected to accommodate a large percentage of such mobile electronic devices 2 enabling the user of such devices to clean the display screen 4 with several strokes.

The invention contemplates several embodiments of constructing the first cleaning portion 30. According to one embodiment, best shown in FIG. 1, such first cleaning portion 30 is constructed as a generally rectangular portion 32, and it is presently preferred for such rectangular portion 32 to be manufactured as a flat and a solid portion 32. The presently preferred size of the rectangular portion 32 is approximately 1 inch in length and approximately 0.38 inches in width.

According to another embodiment, best shown in FIG. 2, the first cleaning portion 30 is constructed as at least a partially peripheral and elongated rod-like frame 34.

The base member 20 further includes an elongated handle portion 40 which extends outwardly from the first cleaning portion 30.

Figure 6:
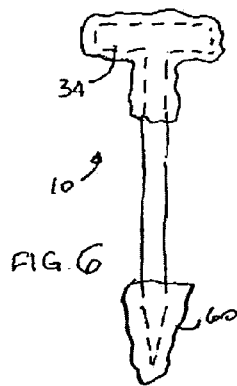
FIG. 6 is a planar view of the cleaning tool for mobile electronic devices, constructed according to yet another embodiment of the invention.
Figure 5:
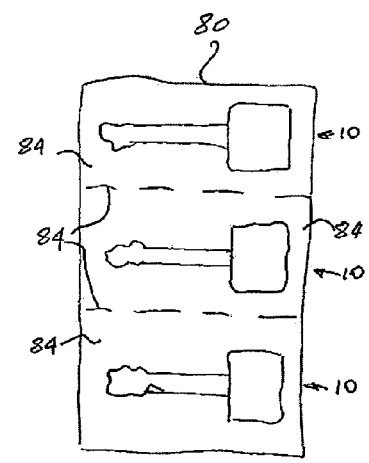
FIG. 5 is a planar view of the cleaning tool of FIG. 1 in combination with a storage means constructed according to one embodiment of the invention.
Figure 7:
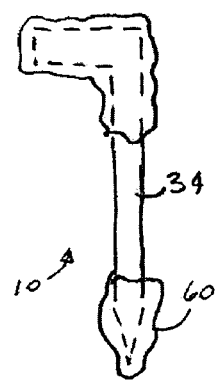
FIG. 7 is a planar view of the cleaning tool for mobile electronic devices, constructed according to a further embodiment of the invention.

In addition to the shapes shown in FIGS. 1-2, the cleaning tool 10 may have a T-shape, as best shown in FIG. 6, an L-shape, as best shown in FIG. 7, or any other shape that may be advantageous for cleaning the mobile electronic device 2.

The cleaning tool 10 further includes a cleaning member 50 which is manufactured from a second predetermined material. Such second predetermined material is preferably cotton of a type presently used in manufacturing of cleaning swabs and which provides for a lint-free cleaning of the display screen 4 and the camera lens 6 and which facilitates economical manufacturing of such cleaning tool 10. When required, an optical grade chamois-like material may be employed in manufacturing of the cleaning member 50.

The cleaning tool 10 additionally includes an adhesive means 38 for attaching the cleaning member 50 to the cleaning portion 30 of the base member 20 in a predetermined pattern.

According to one embodiment of the invention, the cleaning member 50 is attached to and encases at least one edge of the cleaning portion 30 of the base member 20.

According to the presently preferred embodiment of the invention, the cleaning member 50 is attached to each of the pair of opposed surfaces of the rectangular portion 32 and encases at least one edge thereof.

The elongated handle portion 40 has a free end thereof being adapted with a taper 42 which tapers at a predetermined angle away from the first cleaning portion 30 to form a generally sharp end point which is advantageous for use in cleaning recessed type lens 6.

The cleaning tool 10 further includes a second cleaning member 60 which surrounds the free end of the handle portion 40. The presently preferred material of the second cleaning member 60 is cotton which is attached to the free end of the elongated handle portion 40 with any well known method presently used in manufacturing of cleaning swabs.

The present invention contemplates impregnating at least the cleaning members 50 with a predetermined cleaning solution for applications wherein fatty substances such as grease is accumulated on the display screen 4. For example, such predetermined cleaning solution may be of the type presently used for cleaning computer display screens or optical lenses. When the cleaning members 50 is impregnated with such predetermined cleaning solution, the cleaning tool 10 further includes a hermetically sealed sleeve 70 which at least encases the cleaning member 50 to preserve such predetermined cleaning solution during storage. It would be appreciated that the sleeve 70 will be extended to encase the entire cleaning tool 10 when the second cleaning member 60 is also impregnated with such predetermined cleaning solution.

The cleaning tool 10 is further provided with storage means 80 for holding a predetermined plurality of cleaning tools 10. The invention contemplates that the storage means 80 may be of any well known type presently utilized for storing and dispensing products such as cotton swabs, razor blades and the like. By way of example of FIG. 5, the storage means 80 is illustrated as having a plurality of sections 82 manufactured from a clear plastic material, each section being separated from an adjacent one with perforations 84 to store a plurality of cleaning tools 10 being individually sealed.

The invention contemplates that the cleaning tool 10 may be attached directly to the mobile electronic device 2 or to its protective or carrying case (not shown).

Although the present invention has been illustrated in terms of the cleaning tool 10 for use with a mobile phone, it will be apparent to those skilled in the art, that the present invention may be applied to other mobile electronic devices having the display screen 4 and/or camera lens 6.

Furthermore, the cleaning tool 10 of the present invention is suitable for cleaning remaining portions of such mobile electronic device 2, for example such as functional key and alpha-numeric pad 8.

The overall length of the cleaning tool 10 is presently preferred to be about 2.0 inches.

Thus, the present invention has been described in such full, clear, concise and exact terms as to enable any person skilled in the art to which it pertains to make and use the same. It will be understood that variations, modifications, equivalents and substitutions for components of the specifically described embodiments of the invention may be made by those skilled in the art without departing from the spirit and scope of the invention as set forth in the appended claims.

I claim:

1. In combination with a mobile electronic device a cleaning tool for cleaning at least one of a display and a camera lens provided within said mobile electronic device, said tool comprising:
    (a) a planar base member manufactured from a first predetermined material and having a rectangular cleaning portion and an elongated handle portion which is attached to and extends from a longer edge of said cleaning portion, said elongated handle portion having a free end thereof tapering at a predetermined angle to form a generally sharp end point;
    (b) a first cleaning member manufactured from a second predetermined material and attached to said cleaning portion, said first cleaning member is sized for cleaning said display of said mobile electronic device; and
    (c) a second cleaning member manufactured from a third predetermined material and attached to said free end of said elongated handle, said second cleaning member is sized for cleaning said camera lens of said mobile electronic device.

2. The tool, according to claim 1, wherein each of said second predetermined material and said third predetermined material is cotton.

3. The tool, according to claim 1, wherein said tool further includes a preselected storage means.

4. The tool, according to claim 3, wherein storage means includes a plurality of sections which are detachably joined to each other with perforations to store a plurality of said cleaning tools in individually sealed fashion.

* * * * *